United States Patent [19]

Satek et al.

[11] Patent Number: 5,227,530

[45] Date of Patent: Jul. 13, 1993

[54] ALCOHOL CONVERSION USING COPPER CHROMIUM ALUMINUM BORATE CATALYSIS

[75] Inventors: Larry C. Satek; Patrick E. McMahon, both of Wheaton, Ill.

[73] Assignee: Amoco Corporation, Chicago, Ill.

[21] Appl. No.: 856,483

[22] Filed: Mar. 24, 1992

Related U.S. Application Data

[63] Continuation of Ser. No. 705,743, May 28, 1991, abandoned.

[51] Int. Cl.$^5$ .............................................. C07C 45/00
[52] U.S. Cl. ..................................... 568/322; 568/361;
568/406; 568/425; 568/420; 568/485; 568/489
[58] Field of Search ............... 568/404, 405, 406, 401,
568/322, 361, 425, 420, 485, 489

[56] References Cited

U.S. PATENT DOCUMENTS

| | | | |
|---|---|---|---|
| 2,891,095 | 6/1959 | Opitz et al. | 568/406 |
| 3,360,567 | 12/1967 | Johnson | 568/405 |
| 4,141,919 | 2/1979 | Gremmelmaier | 568/405 |
| 4,380,673 | 4/1983 | Bournonville et al. | 568/406 |
| 4,453,015 | 6/1984 | Slaugh et al. | 568/406 |
| 4,645,753 | 2/1987 | Zletz et al. | 502/207 |
| 4,729,979 | 3/1988 | Zletz | 502/204 |
| 4,755,497 | 7/1988 | De Simone et al. | 502/202 |

FOREIGN PATENT DOCUMENTS 782297 2/1984 U.S.S.R. .............................. 568/406

Primary Examiner—James H. Reamer
Attorney, Agent, or Firm—Thomas E. Nemo; Wallace L. Oliver; Frank J. Sroka

[57] ABSTRACT

Conversion of alcohol to organic compounds which comprises contacting the alcohol with a heterogeneous catalyst composition comprising crystalline $$Cu_{2-x}Cr_yAl_{6-y}B_4O_{17}M_mM'_n$$

where M is a divalent metal, M' is a monovalent metal, m is a number in a range from 0 to 0.8, n is a number in a range from 0 to 1.6, X is a number in a range from 0 to 10 0.8 and is equal to the sum of m and n/2, and y is a number in a range from 0.01 to 3, having a characteristic X-ray diffraction pattern.

10 Claims, No Drawings

ALCOHOL CONVERSION USING COPPER CHROMIUM ALUMINUM BORATE CATALYSIS

This is a continuation of application Ser. No. 07/705,743, filed May 28, 1991, now abandoned.

BACKGROUND OF THE INVENTION

The present invention relates to the chemical conversion of alcohol to useful organic compounds which comprises contacting the alcohol with a heterogeneous catalyst composition containing at least copper, chromium, aluminum, boron and oxygen. More particularly, the present invention relates to a process of converting an alcohol to an aldehyde, or a ketone, by contacting the alcohol with a heterogeneous catalyst composition comprising crystalline $$Cu_{2-x}Cr_yAl_{6-y}B_4O_{17}M_mM'_n$$

where M is a divalent metal, M' is a monovalent metal, m is a number in a range from 0 to 0.8, n is a number in a range from 0 to 1.6, X is a number in a range from 0 to 0.8 and is equal to the sum of m and n/2, and y is a number in a range from 0.01 to 3, having a characteristic X-ray diffraction pattern.

Alcohols, which are among the earliest known organic compounds, are derivatives of hydrocarbons in which a hydrogen is replaced by one or more OH group. Numerous processes and catalysts have been used to convert alcohols to aldehydes, and/or ketones. However, there is always a need for new catalysts for these reactions.

The use of an active metallo element or a supported metallo element composition containing aluminum and boron as a conversion catalyst is known in the art. U.S. Pat. No. 3,883,442 to McArthur is illustrative of prior art disclosing the superiority of a supported active metal catalyst to resist shrinkage at high temperatures (up to 1600° C.) by stabilization of a preformed alumina catalyst support. McArthur states stabilization was achieved by impregnating an alumina support with a solution of a boron compound which is thermally decomposable to $B_2O_3$, followed by drying and calcining of the impregnated support at temperatures below about 1500° C., but sufficiently high to decompose the boron compound. McArthur also discloses that the most commonly used technique of preparing a supported metallo element catalyst involved, following calcination, impregnating in conventional manner the alumina support material containing some retained $B_2O_3$ with a solution of the desired metal salt, preferably those that are thermally decomposable to give the corresponding metal oxides and/or sulfides, and calcining the salt-impregnated support to convert the impregnated salt to the active catalytic form. McArthur neither discloses nor suggests a crystalline phase oxide composition of copper, aluminum, and boron, in which any part of the aluminum is replaced by chromium.

Zletz in U.S. Pat. No. 4,729,979, which is hereby incorporated by reference, discusses the characteristics of a good catalyst and/or catalyst support and a new crystalline copper aluminum borate characterized by a specific X-ray diffraction pattern, surface area and pore volume which is at least partially reducible with hydrogen at a temperature no more than 350° C. to a composition containing zero valent copper. Satek in U.S. Pat. No. 4,590,324, which is hereby incorporated by reference, discusses using the new crystalline copper aluminum borate as a catalyst to dehydrogenate alkylaromatics to alkenylaromatics. Zletz et al. in U.S. Pat. No. 4,645,753, which is hereby incorporated by reference, discusses doping the new crystalline copper aluminum borate to contain an alkali metal or alkaline earth metal element for use as a catalyst to dehydrogenate alkylaromatics to alkenylaromatics. The Zletz, Satek, and Zletz et al. patents alone or in combination neither disclose nor suggest a mixed oxide composition of aluminum, boron, and a metallo element without copper.

The general object of the present invention is to provide a new process for the chemical conversion of alcohol to useful organic compounds. Other objects and advantages of the invention will become apparent upon reading the following detailed description and appended claims.

SUMMARY OF THE INVENTION

In one aspect, the present invention is chemical conversion of alcohol to useful organic compounds, such as aldehydes, and ketones, which comprises contacting the alcohol with a heterogeneous catalyst composition comprising copper, chromium, aluminum, boron, oxygen, the heterogeneous catalyst composition having an X-ray diffraction pattern comprising significant lines substantially as described in Table I. As indicated below, catalysts used in this invention are the subject of commonly assigned application Ser. No. (705,742) filed on even date in the name of Satek and McMahon.

In another aspect, the invention is conversion of alcohol to aldehydes or ketones, which comprises contacting the alcohol with a heterogeneous catalyst composition comprising crystalline inorganic material having a formula $$Cu_{2-x}Cr_yAl_{6-y}B_4O_{17}M_mM'_n$$

where M is a divalent metal, M' is a monovalent metal, m is a number in a range from 0 to 0.8, preferably 0.01 to 0.4, n is a number in a range from 0 to 1.6, preferably 0.01 to 1, X is a number in a range from 0 to 0.8, preferably 0.01 to 0.5, and is equal to the sum of m and n/2, and y is a number in a range from 0.01 to 3, preferably 0.015 to 2, and having a characteristic X-ray diffraction pattern comprising significant lines and assigned strengths substantially as shown in Table I.

In another aspect, the invention is conversion of alcohol to aldehydes or ketones, which comprises contacting the alcohol with a heterogeneous catalyst composition comprising an inorganic crystalline material having an X-ray diffraction pattern comprising significant lines substantially as described in Table I, and having a formula $$Cu_{2-x}Cr_yAl_{6-y}B_4O_{17}M_x$$

where M is a divalent metal selected from the group consisting of palladium zinc, cobalt, and nickel, X is a number in a range from 0 to 0.8, preferably 0.01 to 0.5, and y is a number in a range from 0.01 to 3, preferably 0.015 to 2,.

In still another aspect, the invention is conversion of alcohol to aldehydes, and/or ketones, which comprises contacting the alcohol with a heterogeneous catalyst composition comprising an inorganic crystalline material having an X-ray diffraction pattern comprising significant lines substantially as described in Table I, and having a formula $$Cu_2Cr_yAl_{6-y}B_4O_{17}$$

where y is a number in a range from 0.01 to 3, preferably 0.015 to 2.

TABLE I

| Principal XRD Lines | |
|---|---|
| Interplanar Spacing d,[1] Å | Assigned Strength |
| 5.29 ± .05 | Very Strong |
| 5.00 ± .05 | Strong |
| 3.73 ± .03 | Weak-Medium |
| 2.64 ± .03 | Medium Strong |
| 2.61 ± .02 | Weak-Medium |
| 2.50 ± .02 | Weak-Medium |
| 2.26 ± .02 | Weak-Medium |
| 2.16 ± .02 | Medium |
| 2.07 ± .02 | Medium |
| 1.97 ± .02 | Medium |
| 1.86 ± .01 | Weak-Medium |
| 1.81 ± .01 | Medium |

[1]Angstroms

As is generally known, the assigned strengths in X-ray diffraction patterns may vary depending upon the characteristics of the sample. The observed line strength in any particular sample may vary from another sample, for example, depending upon the amount of each crystalline phase and/or amorphous material in a sample. Also, X-ray diffraction lines of a particular crystalline material may be obscured by lines from other materials present in a measured sample.

DETAILED DESCRIPTION OF THE INVENTION

Catalysts useful in this invention comprise crystalline copper chromium aluminum borate. While these catalysts can be prepared by any method (e.g., by calcining a mixture of a source of copper(II) ions, a source of chromium(III) ions, a source of alumina, and a source of boria) the preferred catalysts are produced by forming a dispersion in a liquid medium of a source of copper(II) ions, a source of chromium(III) ions, a source of alumina, and a source of boria, adjusting the pH, if necessary, to gel the mixture, then removing substantially all the liquid from the mixture, and calcining the substantially dry solid mixture. The preferred crystalline copper chromium aluminum borates are disclosed and claimed in commonly assigned application Ser. No. (705,742) filed on even date in the name of Satek and McMahon, the disclosure of which is hereby incorporated by reference.

Conditions of calcination include a temperature within the range of about 600° C. to about 1500° C., and a reaction time that is sufficient to effect formation of a crystalline copper chromium aluminum borate. Calcination may be carried out under vacuum, but a pressure of at least about one atmosphere is generally more suitable. Increasing pressure and temperature of calcination generally affect formation of a crystalline copper chromium aluminum borate in a shorter reaction time. Higher temperatures of calcination typically results in crystalline materials with less desirably surface properties, for example low surface area. Preferred calcination temperatures are in a range of about 700° C. to 1100° C. Calcination can be carried out in air, nitrogen or other inert gases. A preferred atmosphere for calcination contains oxygen.

As indicated above, the heterogeneous catalyst useful in this invention can be prepared generally by dispersing the required ingredients in a liquid medium, preferably an aqueous or aqueous/organic medium which is converted to a gel, removing substantially all the liquid to form superficially dry mixture, and calcining the dry mixture.

When a liquid medium is used, the source of chromium(III) ions can be a sol or any reasonably soluble salt of chromium(III) ions, or precursor thereof which is at least partially soluble in the dispersing liquid, such as the acetate, formate, nitrate, carbonate, chloride, bromide, sulfate and the like. Salts of chromium containing a decomposable anion such as chromium nitrate, chromium acetate, chromium formate, chromium carbonate, chromium alkoxide, etc. are preferred. When the source of chromium is a sol, oxides are preferred.

Typically, best results are obtained when each of the sources used is chosen to reduce to content of foreign anions and cations in the reaction mix.

In order to avoid the introduction of any extraneous ions into the crystalline copper chromium aluminum borate, it is generally desirable to avoid the presence of cations or anions that are not destroyed and/or volatilized during the subsequent drying and/or calcination step. The presence of volatile components in preparation of copper chromium aluminum borate, such as water, ammonia, acetate ion, nitrate ion, etc. is advantageous in providing the copper chromium aluminum borate with relatively high surface area and porosity desirable for most catalytic reactions.

Accordingly, sources of copper for use in this invention include copper nitrate, copper acetate, copper carbonate, copper borate, etc. since the nitrate, acetate or carbonate anions are destroyed during the drying or calcination step.

The source of alumina is any material capable of producing alumina, but preferred is a well dispersed, liquid source such as an alumina sol.

The source of boria is a material such as borate, boron oxide, or boric acid with pure boric acid being preferred.

Typically, the molar ratios of the various reactants can be varied to produce the solid of this invention. Specifically, the molar ratios in terms of oxides of the initial reactant concentrations are characterized by the general mixed oxide formula $$(u)CuO \cdot (v)Cr_2O_3 \cdot (w)Al_2O_3 \cdot (k)B_2O_3$$

where u, v, w, and k are numbers representing molar amounts of the oxides of the source reagents. The molar ratios of $CuO/B_2O_3$, calculated as u/k, are about 0.2 to about 5, preferably about 0.5 to about 2, and most preferably about 0.67 to about 1.5, the molar ratios of $(Cr_2O_3+Al_2O_3)/B_2O_3$, calculated as (v+w)/k, are about 0.3 to about 20, preferably about 0.5 to about 6, and most preferably about 1 to about 3, and the molar ratios of $Al_2O_3/(Cr_2O_3+Al_2O_3)$, calculated as w/(v+w), are from about 0.3 to about 20, preferably about 0.5 to about 6, and more preferably about 1 to about 3.

In somewhat greater detail, a preferred procedure is to dissolve the boria source and disperse the alumina source in water with mixing in a blender for about 3–5 minutes, then add an aqueous sol or solution of a source of a copper and an aqueous sol or solution of a source of chromium to the blender followed by gelation with a chemical base such as ammonia or tetramethylammonium hydroxide.

Typically, the pH of the aqueous mixture is less than about 11. If the reaction media is too acid or too basic, the desired solid generally will not form or other contaminating phases are formed in addition to the desired product. To some extent the pH of the reaction mixture controls surface properties of the final calcined solid material. Preferably, the pH of the reaction mixture is in a range from about 2 to about 10, more preferably about 3 to about 9, in order to gel the reaction mixture. If desired, the pH can be adjusted with a base such as ammonia, ethylenediamine, tetramethylammonium hydroxide and the like. Preferred is the use of ammonium hydroxide. The presence of the ammonia as well as other volatile components in the gelled mixture, such as acetate ion, nitrate ion, etc., is advantageous in providing the final calcined solid with sufficiently high surface area and porosity desirable for catalytic reactions.

The gelled mixture is allowed to air-dry, usually for about 1-3 days, followed by vacuum drying, typically at a pressure of about 0.3 atmosphere for about 15 to 25 hours at about 100° C. to 150° C. with a purge of dry gas, such as nitrogen.

The superficially dry mixture is calcined, preferably at a temperature within the range of about 700° C. to about 1000° C. for a reaction time that is sufficient to effect formation of a crystalline metalloaluminum borate, typically a reaction time within the range of about 2 to about 30 hr. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° C. to about 225° C., to form a dry cake which can then be treated as required for its intended use.

The solid materials made for use in this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

Advantageously, a crystalline copper chromium aluminum borate for use according to this invention is formed or combined with from about 0.05 to about 50 wt % of at least one compound of a metallo element based on the weight of crystalline material.

A suitable metallo dopant is selected from the group consisting of alkali metal, alkaline earth metal, low melting metal, brittle metal, and heavy metal compounds which include their oxides, hydroxides and salts of lithium, sodium, potassium, rubidium, cesium, magnesium, calcium, strontium, barium, chromium, zinc, cadmium, lanthanum, cerium, palladium, platinum, and thorium. Suitable compounds include lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium and palladium, in the form of the oxide or in a form readily convertible to the oxide, are preferred. The solid materials formed according to this invention can be treated with from about 0.05 to 50 wt % dopant based on the weight of the solid material. The metallo compound or compounds can be dry-blended with the copper chromium aluminum borate, dissolved in a suitable solvent, preferably water, mixed with the solid material and dried; or aqueous solutions of same can be added to feedstocks going to a reactor containing the solid material catalyst.

Particularly useful is the fact that when these solid catalyst compositions are used in liquid and/or gas phase processes, the products of chemical conversion are easily separated from the solid catalyst material. Also useful is the fact that when these solid catalyst compositions are used in such fluid-phase processes, the active metallo element components are only slowly extracted, leading to longer catalyst lifetime.

Alcohol conversion processes are well known in the art and numerous processes with and without added oxygen and with numerous catalysts are described in various U.S. and foreign patents and publications.

The following examples will serve to illustrate certain specific embodiments of the herein disclosed invention. These examples should not, however, be construed as limiting the scope of the novel invention, as there are many variations which may be made thereon without departing from the spirit of the disclosed invention, as those of skill in the art will recognize.

The alcohols useful in this invention include monohydric alcohols, e.g., primary and secondary alcohols, and polyhydric alcohols having normal boiling points up to a temperature of about 300° C. Particularly useful are alcohols having 2 to about 12 carbon atoms. Of these, the preferred alcohols are ethyl alcohol (ethanol), isopropyl alcohol (2-propanol), cyclohexanol and sec-butyl alcohol (2-butanol).

Generally a process of the present invention for chemical conversion of alcohol to useful organic compounds comprises contacting under suitable reaction conditions an alcohol in a fluid phase, i.e., liquid and/or vapor phase, with a heterogeneous catalyst composition.

The alcohol conversion process of this invention is carried out on a continuous basis in either a fixed bed mode of operation or in a fluidized bed at a temperature between about 100° and 400° C., preferably 120° to 375° C., most preferably about 130° to 300° C. at a pressure of about ½ atmospheric to about 5,000 psig or higher, preferably about 0 to about 3,000 psig.

It will be understood that the contact time for gas phase reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

As indicated, the organic reactant contains an alcohol, preferably lower monohydric alcohol, e.g., 2 to 12 carbon atoms such as ethyl, propyl, butyl, amyl alcohols, and cyclohexanol in an amount upward from about 10 percent, preferably from 75 to about 100 percent of the organic reactant. The reactant feed stream can, of course, contain other materials, as for example, the inert gas diluents, e.g., nitrogen, recycled intermediates and possibly some small amounts of other by-products associated with the recycle stream. This use of a recycle stream will make possible a still more efficient process.

In addition to the above required parameters of the process it is essential that a particular type of material be used as catalyst. Preferred is a heterogeneous catalyst composition comprising crystalline inorganic material having a formula $$Cu_{2-x}Cr_yAl_{6-y}B_4O_{17}M_mM'_n$$

where M is a divalent metal, M' is a monovalent metal, m is a number in a range from 0 to 0.8, preferably 0.01 to 0.4, n is a number in a range from 0 to 1.6, preferably 0.01 to 1, X is a number in a range from 0 to 0.8, preferably 0.01 to 0.5, and is equal to the sum of m and n/2, and y is a number in a range from 0.01 to 3, preferably 0.015 to 2, and having a characteristic X-ray diffraction pattern comprising significant lines and assigned strengths substantially as shown in Table I.

In particular, the present invention has been used for chemical conversion reactions such as dehydrogenation of ethanol to acetaldehyde, for dehydrogenation of cumene to alpha-methylstyrene, and for dehydrogenation of 1-propanol to propionaldehyde, isopropyl alcohol to acetone, and cyclohexanol to cyclohexanone.

The following examples will serve to illustrate certain specific embodiments of the herein disclosed invention. These examples should not, however, be construed as limiting the scope of the novel invention, as there are many variations which may be made thereon without departing from the spirit of the disclosed invention, as those of skill in the art will recognize.

EXAMPLES

General

Temperatures are in degrees Celsius.
Percents are weight percents.

EXAMPLE 1

In this example about 25 molar percent of the aluminum oxide is replaced by chromium oxide. Specifically, the copper chromium aluminum borate is characterized by the formula $$Cu_2Cr_{1.25}Al_{4.5}B_4O_{17}$$

This crystalline copper chromium aluminum borate was prepared as follows: PHF alumina sol (763.8 g of a 7.51% $Al_2O_3$ sol, 0.562 mol) was added to a 1 gal blender. Chromium nitrate hexahydrate (89.3 g, 0.375 mol), without any additional water, was added to the blender and blended until dissolved. Copper nitrate hexahydrate (116.3 g, 0.50 ml) was dissolved in 200 mL warm deionized water and added to the blender. Boric Acid (61.8 g, 1.00 mol) was dissolved in 350 mL warm deionized water and also added to the blender. The mixture was blended for an additional two minutes until the thin mixture was homogeneous and deep blue. The pH of the mixture at this point was 1.94. Then 700 mL of a 20% ammonium hydroxide in methanol solution was added while blending, to give a thick gel having a final pH of 7. The gel was placed on 35×45 cm plastic trays for drying. The material was vacuum dried (0.3 atm., nitrogen flow) for 4 hours at 180° C. At this temperature, the sample appeared to be overheating, and the nitrogen flow was turned up and the heat turned off. A 40 g portion of the material was calcined with the following program.

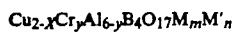

$$25° C. \xrightarrow{2\ hr} 175° C. \xrightarrow{12\ hr} 400° C. \xrightarrow{4\ hr}$$

$$830° C. \xrightarrow{8\ hr} 830° C. \xrightarrow{4\ hr} 250° C. \longrightarrow RT$$

The surface area was determined to be 5 m²/g. The material was analyzed by ICP and found to contain 8.0% Cr, 21.5% Al, 21.6% Cu and 6.6% B. The XRD powder pattern shows that the material is highly crystalline with only the copper aluminum borate XRD powder pattern observed. The powder X-ray diffraction lines of this crystalline copper chromium aluminum borate are set out below:

| Interplanar Spacing d,[1] Å | Assigned Strength[2] | Relative Intensity |
|---|---|---|
| 7.051 | M | 23 |
| 5.31 | VS | 100 |
| 5.03 | S | 56 |
| 3.75 | W-M | 6 |
| 3.64 | VW-W | 3 |
| 3.36 | W | 7 |
| 3.01 | VW-W | 2 |
| 2.85 | MVW-W | 4 |
| 2.65 | M-S | 33 |
| 2.62 | W-M | 10 |
| 2.51 | W-M | 10 |
| 2.27 | W-M | 15 |
| 2.17 | W-M | 12 |
| 2.08 | W-M | 12 |
| 1.99 | M | 24 |
| 1.87 | VW-W | 6 |
| 1.82 | VW-W | 8 |
| 1.77 | VW | 3 |
| 1.68 | W-M | 9 |
| 1.60 | VW-W | 3 |
| 1.57 | VW-W | 3 |

[1] Angstroms
[2] VW = very weak; W = weak; M = medium; S = strong; VS = very strong Unit cell volumes are calculated from the unit cell dimensions, which are determined from the indexed powder patterns—a normal analytical procedure for analysis of XRD powder patterns.

The material was indexed on the tetragonal cell and the cell parameters were compared to the best single crystal and powder data of pure copper aluminum borate. Standard deviations are in parentheses.

| source | a and b, Å | c, Å | volume, Å³ |
|---|---|---|---|
| Example 1 | 10.6280 | 5.7158 | 645.6 |
| $Cu_2Al_6B_4O_{17}$ | 10.5736 | 5.6703 | 633.9 |

The nature of the unit cell volume changes upon the synthesis of solid solutions is described in standard inorganic texts such as "Structural Inorganic Chemistry" Vol. 5, A. F. Wells, Clarendon Press, Oxford, 1984, p.

1294. "For two element in the same group in our classification the range of composition over which solid solutions are formed depends on the relative sizes of the two atoms. This is to be expected, since if some of the atoms in a structure are replaced (at random) by others of a different size, distortion of the structure must occur and the cell dimensions alter as the concentration of the solute increases. To a first approximation they vary linearly with the atomic percentage of the solute (Vegard's law), though in many cases this law is not exactly obeyed."

EXAMPLE 2

In this example about 5 molar percent of the aluminum oxide is replaced by chromium oxide. Specifically, the copper chromium aluminum borate is characterized by the formula $$Cu_2Cr_{0.3}Al_{5.7}B_4O_{17}$$

This crystalline copper aluminum borate was prepared as follows: PFH alumina sol (347.5 g of a 7.51 percent $Al_2O_3$ sol, 0.285 mole) was added to the blender, and without any additional water, was mixed until dissolved. Copper nitrate hexahydrate (46.7 g, 0.030 mole) was dissolved in 50 mL warm deionized water and added to the blender. Boric acid (24,86 g, 0.40 mole) was dissolved in 120 mL deionized water and also added to the blender. The mixture was blended for an additional two minutes until the thin mixture was homogeneous and deep blue. The pH was 1.94. A total of 210 mL of a 20 percent ammonium hydroxide in methanol solution was added, with blending, to give a thick gel whose final Ph was 7. The gel was placed on 35×45 cm plastic trays for drying. The material was vacuum dried (0.3 atm., nitrogen flow, for 17 hours at 120° C.). The material was calcined with the following program.

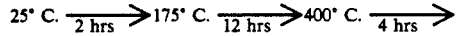

The surface are was determined to be 28.8 m²/g. The XRD powder pattern shows that the material is highly crystalline with only the copper aluminum borate XRD powder pattern observed. The material was indexed on the tetragonal cell, and the cell volume is determined to be 637 Å³.

EXAMPLE 3

In this example about 10 molar percent of the aluminum oxide is replaced by chromium oxide. Specifically, the copper chromium aluminum borate is characterized by the formula $$Cu_2Cr_{0.6}Al_{5.4}B_4O_{17}$$

This crystalline copper aluminum borate was prepared as follows: PHF alumina sol (916.75 g of a 7.51 percent $Al_2O_3$ sol, 0.712 mole) was added to a 1-gallon blender. Chromium nitrate hexahydrate (23.81 g, 0.076 mole) was added to the blender, and without any additional water, was mixed until dissolved. Copper nitrate hexanhydrate (116.1 g, 0.50 mole) was dissolved in 50 mL warm deionized water and added to the blender. Boric acid (61.8 g, 1.00 mole) was dissolved in 120 mL warm deionized water and also added to the blender. The mixture was blended for an additional two minutes until the thin mixture was homogeneous and blue-green. A total of 1000 mL of a 20 percent ammonium hydroxide in methanol solution was added, with blending, to give a thick gel whose final pH was 7.8. The gel was placed on 35×45 cm plastic trays for drying. The material was vacuum dried (0.3 atm., nitrogen flow, for 17 hours at 120° C.). The material was calcined with the following program:

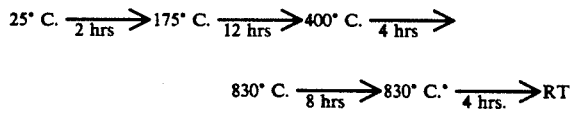

The surface area was determined to be 50.4 m²/g. A copy of the XRD powder pattern shows that the material is crystalline with only the copper aluminum borate XRD powder pattern observed. The material was indexed on the tetragonal cell and the cell volume is determined to be 639 A3. Inductively coupled plasma (ICP) analysis shows percent Al 36.0, percent Cu 12.9, percent Cr 2.46.

EXAMPLE 4

In this example about 25 molar percent of the aluminum oxide is replaced by chromium oxide, with palladium doping.

This catalyst was prepared as follows: PHF alumina sol (1528 g of a 7.51 percent $Al_2O_3$ sol, 1.125 mole) was added to a 1-gallon blender. Chromium nitrate hexahydrate (179 g, 0.759 mole) was added to the blender, and without any additional water, was mixed until dissolved. Copper nitrate hexahydrate (230.3 g, 0.99 mole) was dissolved in 250 mL warm deionized water along with palladium nitrate (2.36 g, 0.01 mole) and added to the blender. Boric acid (61.8 g, 1.00 mole) was dissolved in 120 mL warm deionized water and also added to the blender. The mixture was blended for an additional two minutes until the thin mixture was homogeneous and teal blue. A total of 18000 mL of a 20 percent ammonium hydroxide in methanol solution was added, with blending, to give a thick gel whose final pH was 6.3. The gel was placed on 35×45 cm plastic trays for drying. The material was vacuum dried (0.3 atm., nitrogen flow, for 17 hours at 120° C.). The material was calcined with the following program:

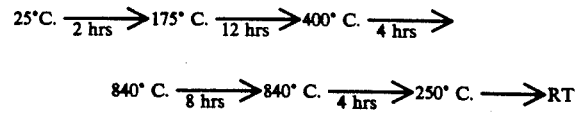

Inductively couple plasma (ICP) analysis shows percent Al 20.1, percent Cu 25.5, percent Cr 9.1.

A portion of the above sample, 88 g of 20/35 mesh material, was impregnated with potassium by incipient wetness using potassium carbonate. Potassium carbonate (11.4 g) was dissolved in 30 mL deionized water and added to the sieved material with an eyedropper. The sample was allowed to dry. The sample was calcined in an oven for 6 hours at 400° C.

In the following examples crystalline copper chromium aluminum borate catalysts are employed for alcohol dehydrogenation.

General Alcohol Dehydrogenation Experimental Procedures

EXAMPLES 5 AND 6

A fixed volume of catalyst was loaded into a gas phase reactor system comprising a liquid pumping system, preheat coil, metal tube heated by tube furnace, and an effluent system fitted to allow automatic sampling to an on-line gas chromatograph. Isopropyl alcohol or n-propanol were fed into the reactor such that the liquid hourly spaced velocity remained constant at 5.2 for each catalyst tested. The temperature of the reactor was then adjusted to achieve approximately 50% conversion for each catalyst. Samples were automatically collected and analyzed using standard GC techniques. Some catalysts were left on stream for several weeks to monitor deactivation rates.

EXAMPLES 10 AND 12

In the general procedure, a 300 ml three-neck round bottom flask was fitted with a reflux condenser, thermometer, and stirring apparatus. A 150 gram amount of 2-phenethyl alcohol solid or o-nitrobenzyl alcohol was placed in the flask. To this were added 3 grams of the specific catalyst. The contents of the flask were then heated to the desired temperature, the dehydrogenation thus being performed in the alcohol melt phase. The reaction was continued while intermittent samples were taken to determine conversion and product distribution. In theory, the reactions can be pushed to completion because co-product hydrogen escapes the reaction mixture.

EXAMPLES 7, 8, 9 AND 11

Gas phase reactors fitted with regulated pumping systems, three-zone heating furnaces, fixed-bed tube reactors, and a refrigerated liquid collecting system were used for these experiments. Catalyst requirements were 40–70 grams. Liquid products were collected and analyzed by gas chromatographic/mass spectroscopic techniques.

EXAMPLE 5

Dehydrogenation of 2-Propanol[1]

| Catalyst | Hrs. | Temp. | Conv. | Propene | Acetone | Condens. Products |
|---|---|---|---|---|---|---|
| Example 1 | 30 | 160 | 50.1 | 0 | 98.8 | 1.2 |
|  | 100 |  | 47.7 | 0 | 98.4 | 1.6 |
|  | 200 |  | 50.4 | 0 | 98.7 | 1.3 |
|  | 280 |  | 49.1 | 0 | 98.8 | 1.2 |
| chromium free[2] | 42 | 150 | 48.2 | 1.3 | 97.2 | 1.5 |
|  | 118 |  | 47.2 | 1.9 | 95.4 | 2.7 |
| chromium free[3] | 17 | 145 | 49.1 | 0 | 95.9 | 4.1 |
|  | 100 |  | 46.7 | 0.2 | 97.3 | 2.5 |
|  | 200 |  | 37.5 | 0.2 | 98.8 | 1.0 |
|  | 300 |  | 33.1 | 0 | 99.3 | 0.7 |

[1]LHSV 5.2
[2]Cu$_2$Al$_6$B$_4$O$_{17}$ made at final gel pH 7.5
[3]Cu$_2$Al$_6$B$_4$O$_{17}$ made at final gel pH 9.5

EXAMPLE 6

Dehydrogenation of 1-Propanol[1]

| Catalyst | Hrs. | Temp. | Conv. | Propene | Propanal | Condens. Products |
|---|---|---|---|---|---|---|
| Example 1 | 30 | 245 | 50.4 | 3.1 | 58.2 | 38.7 |
|  | 50 |  | 45.5 | 2.2 | 68.9 | 28.9 |
|  | 100 |  | 48.3 | 0.5 | 61.1 | 38.4 |
|  | 150 |  | 45.8 | 0.4 | 66.3 | 33.3 |
|  | 200 |  | 46.3 | 0.3 | 73.7 | 26.0 |
|  | 230 |  | 44.8 | 0.3 | 73.8 | 25.9 |
| chromium free[2] | 10 | 255 | 47.5 | 0.5 | 83.5 | 16.0 |
|  | 30 |  | 25.5 | 2.3 | 74.7 | 12.0 |
|  | 50 |  | 26.6 | 1.4 | 75.4 | 12.2 |
|  | 80 |  | 20.9 | 2.0 | 71.5 | 26.5 |
| chromium free[3] | 20 | 260 | 49.4 | 0.5 | 84.6 | 14.9 |
|  | 50 |  | 42.5 | 1.3 | 91.0 | 7.7 |
|  | 70 |  | 39.2 | 1.8 | 91.3 | 6.9 |

[1]LHSV 5.2
[2]Cu$_2$Al$_6$B$_4$O$_{17}$ made at final gel pH 7.5
[3]Cu$_2$Al$_6$B$_4$O$_{17}$ made at final gel pH 9.5

EXAMPLE 7

Dehydrogenation of Cyclohexanol Over Copper Chromium Aluminum Borate[1]

| Temp. | WHSV | Conversion | Cyclohexanone | Cyclohexene | Phenol | Condens. Products |
|---|---|---|---|---|---|---|
| 165 | 1 | 18% | 100% | — | — | — |
| 185 | 1 | 30% | 98% | 1% | — | 1% |
| 205 | 1 | 55% | 85% | 8% | 1% | 6% |
| 205 | 2 | 39% | 99% | 1% | — | — |
| 225 | 1 | 63% | 89% | 7% | — | 4% |

[1]Example 1

EXAMPLE 8

Gas Phase Dehydrogenation of 2-Phenethyl Alcohol[1]

| Catalyst | Temp. | Conv. | Acetophenone | Ethylbenzene plus Styrene |
|---|---|---|---|---|
| Example 1 | 160 | 52% | 64% | 36% |
|  | 175 | 81% | 58% | 42% |
|  | 200 | 98% | 59% | 41% |
| chromium free[2] | 150 | 69% | 57% | 43% |

[1]WHSV 1.0
[2]Cu$_2$Al$_6$B$_4$O$_{17}$ made at final gel pH 9.5

EXAMPLE 9

Gas Phase Dehydrogenation of 1-Phenethyl Alcohol[1]

| Catalyst | Temp. | Conv. | Toluene | Ethylbenzene plus Styrene | 2-phenyl ethanal | Condens. Products |
|---|---|---|---|---|---|---|
| Example 1 | 180 | 10% | 29% | 2% | 45% | 24% |
|  | 200 | 30% | 15% | 5% | 64% | 16% |

[1]WHSV 1.0

EXAMPLE 10

Liquid Phase Dehydrogenation of Benzyl Alcohol

| Catalyst | Temp. | Hours | Conv. | Product Distribution | |
|---|---|---|---|---|---|
| | | | | Benzaldehyde | Toluene |
| Example 1 | 145 +/− 5 | 45 | 38% | 62% | 38% |
| chromium free[2] | 160 +/− 5 | 18 | 14% | 72% | 28% |

[1]WHSV 1.0
[2]$Cu_2Al_6B_4O_{17}$ made at final gel pH 9.5

EXAMPLE 11

Gas Phase Dehydrogenation of Benzyl Alcohol Over Copper Chromium Aluminum Borate[1]

| Temperature | Conversion | Product Distribution | |
|---|---|---|---|
| | | Benzaldehyde | Toluene |
| 150° C. | 12% | 59% | 41% |
| 165° C. | 23% | 53% | 47% |
| 185° C. | 84% | 52% | 48% |
| 205° C. | 95% | 49% | 51% |

[1]WHSV 1.0, Example 1 copper chromium aluminum borate

EXAMPLE 12

Liquid Phase Dehydrogenation of o-Nitrobenzyl Alcohol Over Copper Chromium Aluminum Borate[1]

| Temp. | Hours | Conv. | Product Distribution | | | |
|---|---|---|---|---|---|---|
| | | | o-Nitro-benzaldehyde | Nitro-benzene | N-formyl-aniline plus o-Amino benzaldehyde | Product Dimers |
| 175 +/− 20 | 9 | 38% | 93% | — | 3% | 4% |
| 145 +/− 5 | 30 | 73% | 71% | 3% | 21% | 5% |

[1]WHSV 1.0, Example 1 copper chromium aluminum borate

What is claimed is:

1. The heterogeneous catalytic conversion of alcohol to organic compounds comprising aldehyde and/or ketone dehydrogenation products of the alcohol, which comprises contacting alcohol having a normal boiling point temperature in a range up to about 300° C. with an inorganic crystalline material comprising crystalline copper chromium aluminum borate, having an X-ray diffraction pattern comprising significant lines substantially as follows

| Interplanar Spacing d, Å | Assigned Strength |
|---|---|
| 5.29 ± .05 | Very Strong |
| 5.00 ± .05 | Strong |
| 3.73 ± .03 | Weak-Medium |
| 2.64 ± .03 | Medium Strong |
| 2.61 ± .02 | Weak-Medium |
| 2.50 ± .02 | Weak-Medium |
| 2.26 ± .02 | Weak-Medium |
| 2.16 ± .02 | Medium |
| 2.07 ± .02 | Medium |
| 1.97 ± .02 | Medium |
| 1.86 ± .01 | Weak-Medium |
| 1.81 ± .01 | Medium, | at temperatures in a range from about 100° C. to about 400° C. and pressures in a range from about ½ atmospheric to about 5,000 psig.

2. The process of claim 1 wherein the conversion process is carried out at a temperature in a range from about 120° C. to about 375° C. and pressures in a range from about 0 psig to about 3,000 psig.

3. The process of claim 1 wherein the inorganic crystalline material comprises $$Cu_{2-x}Cr_yAl_{6-y}B_4O_{17}M_mM'_n$$

where M is a divalent metal selected from the group consisting of palladium, zinc, cobalt, and nickel, M' is a monovalent metal selected from the group consisting of lithium, sodium, potassium, rubidium, and cesium, m is a number in a range from 0 to 0.8, n is a number in a range from 0 to 1.6, X is a number in a range from 0 to 0.8 and is equal to the sum of m and n/2, and y is a number in the range from 0.01 to 3.

4. The process of claim 1 wherein the inorganic crystalline material comprises $$Cu_{2-x}Cr_yAl_{6-y}B_4O_{17}M_X$$

where M is a divalent metal selected from the group consisting of palladium, zinc, cobalt, and nickel, X is a number in a range from 0.01 to 0.8, and y is a number in a range from 0.01 to 3.

5. The process of claim 4 wherein the M is zinc.
6. The process of claim 4 wherein the M is cobalt.
7. The process of claim 4 wherein the M is nickel.
8. The process of claim 4 wherein the M is palladium.
9. The process of claim 1 wherein the inorganic crystalline material is a crystalline copper chromium aluminum borate comprising $$Cu_2Cr_yAl_{6-y}B_4O_{17}$$

where y is a number in a range from 0.05 to 2.5.

10. The process of claim 9 wherein the inorganic crystalline material is doped with from about 0.05 to about 50 weight percent of at least one metallo element selected from the group consisting of potassium and palladium based on the weight of catalyst material.

* * * * *